(12) United States Patent
Ben-Haim et al.

(10) Patent No.: US 6,285,906 B1
(45) Date of Patent: Sep. 4, 2001

(54) MUSCLE CONTRACTION ASSIST DEVICE

(75) Inventors: Shlomo Ben-Haim; Nissim Darvish, both of Haifa; Yuval Mika, S. Zichron Yaakov; Benny Rousso, Bat Yam; Bella Felzen, Haifa, all of (IL)

(73) Assignee: Impulse Dynamics N. V., Curacao (AN)

( * ) Notice: Subject to any disclaimer, the term of this patent is extended or adjusted under 35 U.S.C. 154(b) by 0 days.

(21) Appl. No.: 09/320,089

(22) Filed: May 26, 1999

(51) Int. Cl.$^7$ .................................................. A61N 1/36
(52) U.S. Cl. ..................... 607/4; 607/5; 607/14; 607/15
(58) Field of Search ................. 607/4, 5, 14, 15

(56) References Cited

U.S. PATENT DOCUMENTS

| | | | |
|---|---|---|---|
| 5,468,254 | * 11/1995 | Hahn et al. ........................ | 607/5 |
| 5,800,464 | 9/1998 | Kieval . | |
| 5,814,079 | * 9/1998 | Kieval ............................. | 607/4 |

FOREIGN PATENT DOCUMENTS

| | | |
|---|---|---|
| WO 97/25098 | 7/1997 | (WO) . |
| WO 98/02272 | 1/1998 | (WO) . |
| WO 98/10830 | 3/1998 | (WO) . |
| WO 98/10831 | 3/1998 | (WO) . |
| WO 98/10832 | 3/1998 | (WO) . |

* cited by examiner

Primary Examiner—Carl Layno
(74) Attorney, Agent, or Firm—Cowan, Liebowitz & Latman, P.C.; William H. Dippert

(57) ABSTRACT

A method and apparatus for controlling a segment of excitable tissue, typically tissue of a heart, the segment having an intrinsic activity level. During a high phase, electrical energy of a given amplitude is applied to the segment. During a low phase, the amplitude of the electrical energy applied to the segment is reduced relative to that applied during the high phase, so that the segment's activity level increases during the low phase above the intrinsic activity level.

17 Claims, 3 Drawing Sheets

MUSCLE CONTRACTION ASSIST DEVICE

FIELD OF THE INVENTION

The present invention relates generally to invasive devices and methods for treatment of the heart, and specifically to devices and methods for controlling contraction of the heart muscle.

BACKGROUND OF THE INVENTION

The human body normally regulates the cardiac output in response to body needs by changing the heart rate, as during physical exercise, and/or by adapting the stroke volume. Under pathological conditions, however, some of the normal regulatory mechanisms may be damaged. For example, heart tissue damaged due to myocardial infarct typically cannot sustain normal pumping function. Although such damage is local in its direct effect on the heart tissue, it can lead to an overall reduction in stroke volume, and hence of cardiac output. The body may react to such a reduction by increasing the heart rate, thus imposing long term strain on the heart muscles, leading in more severe cases to heart failure. There is thus a need for devices and treatments that can regulate the activity of local areas of the heart, so as to compensate for the deficiencies in the normal regulation mechanisms and aid in recovery from infarct and other damaging conditions, PCT patent application PCT/IL97/00012, and the corresponding U.S. national phase application Ser. No. 09/101,723, which are assigned to the assignee of the present patent application and are incorporated herein by reference, describe methods for modifying the force of contraction of at least a portion of a heart chamber by applying a non-excitatory electrical signal to the heart at a delay after electrical activation of the portion. The signal may be applied in combination with a pacemaker or defibrillator, which also applies an excitatory signal (i.e., pacing or defibrillation pulses) to the heart muscle.

PCT patent application PCT/IL97/00236 and the corresponding U.S. national phase application Ser. No. 09/254,900, which are assigned to the assignee of the present patent application and are incorporated herein by reference, describe a pacemaker that modifies cardiac output. This pacemaker applies both excitatory (pacing) and non-excitatory electrical signals to the heart. By applying non-excitatory signals of suitable strength, appropriately timed with respect to the heart's electrical activation, the contraction of selected segments of the heart muscle can be increased or decreased.

PCT patent application PCT/IL97/00233 and the corresponding U.S. national phase application Ser. No. 09/254,903, which are assigned to the assignee of the present patent application and are incorporated herein by reference, describe methods of applying signals to cardiac tissue in order to modify the behavior thereof.

PCT patent application PCT/IL97/00235, which is incorporated herein by reference, describes a cardiac output controller which applies non-excitatory pulses to the heart in order to increase the heart's stroke volume. Typically, the pulses are timed with respect to the heart's natural activity, and are delivered, for example, during a specific time period of each heart beat.

SUMMARY OF THE INVENTION

It is an object of some aspects of the present invention to provide improved methods and apparatus for regulating contraction of heart muscle.

It is a further object of some aspects of the present invention to provide methods and apparatus for control and enhancement of the contraction of local areas of the heart muscle.

It is yet a further object of some aspects of the present invention to provide improved methods and apparatus for increasing heart output.

In preferred embodiments of the present invention, an electrical cardiac stimulator applies electrical energy to a segment of a patient's heart in successive high and low phases, so that in the low phase, an activity level of the segment increases substantially above an intrinsic activity level thereof. The stimulator comprises one or more electrodes, preferably placed at multiple sites in or on the heart, and a control unit. The energy is applied to the heart via the electrodes at a certain amplitude in the high phase, followed by lower-amplitude or substantially no energy applied during the low phase. Preferably, the patient's overall cardiac output increases responsive to the increase of the segment's activity.

In some preferred embodiments of the present invention, energy is applied to more than one segment, preferably in a coordinated fashion, in order to increase cardiac output. It will be appreciated that, although most preferred embodiments of the present invention are described herein with respect to applying energy to one segment, it is within the scope of the present invention to apply the energy to a plurality of segments.

Preferably, the average power output of muscle tissue exposed to repeated applications of electrical energy, as provided by preferred embodiments of the present invention, is greater than that generated responsive to either standard pacing pulses or natural cardiac activity in an in vivo heart. Thus, application of the energy is appropriate, for example, for assisting a heart that is otherwise unable to satisfy immediate physiological requirements of flow rate and blood pressure. In particular, the energy may be applied to one or more segments of the heart, either in a generally-localized region, which may be a functional or a dysfunctional area of one chamber, or in multiple chambers of the heart. Energy applied to each segment is preferably timed with respect to that applied to the other segments so that during a time period when some segments are exposed to the high phase of the energy, and thus do not contribute substantially to the heart's pumping action, the rest of the heart muscle is generally either contracting normally, or in an enhanced manner responsive to application of the low-phase of the energy.

In some preferred embodiments of the present invention, the control unit administers the electrical energy in the form of "contractility control" signals to at least one of the electrodes. Preferably, the high phase has the general form of rapid pacing pulses and/or "fencing" signals, as described in the above-cited U.S. patent application Ser. No. 09/254,903. Fencing signals, applied through one or more electrodes in a vicinity of the segment, typically alter electrical activity and/or a contraction force of the segment by inhibiting the generation and propagation of an action potential in the segment.

In some of these embodiments, throughout the duration of the high phase, the contraction force generated by muscle of the segment may be significantly reduced. The transition from the high to the low phase engenders a large increase in the contraction force, to a level which is typically significantly higher than prior to application of the high phase. In general, the overall force, integrated over a single high phase and the subsequent low phase, is higher than that which would be attained without the application of the contractility control signals. Repeated application of the contractility control signals, i.e., cycling between the high and low phases, preferably yields an overall increase in cardiac output and/or blood pressure responsive to the behavior of the segment (or of a plurality of stimulated segments) during the low phase.

In some preferred embodiments of the present invention, the electrodes are placed at multiple sites on the epicardium and/or endocardium of the segment of the heart, and optionally on other areas of the heart. Alternatively or additionally, one or more of the electrodes are inserted through a catheter into a blood vessel of or in a vicinity of the heart, and apply energy through the vessel wall to a region of the heart. Further alternatively or additionally, at least one of the electrodes is placed elsewhere in or on the patient's body. Typically, each electrode conveys a particular waveform to the heart, which may differ in certain aspects from the waveforms applied to other electrodes. The particular waveform to be applied to each electrode is preferably determined by the control unit under the control of a human operator during an initial calibration period of the unit. Further preferably, the cardiac stimulator (or elements thereof) is implanted in the patient in a manner similar to that used to implant pacemakers or implantable defibrillators known in the art, such that after the initial calibration period, the unit is generally able to automatically modify the waveforms as needed to maintain a desired level of performance of the stimulator.

In a preferred embodiment, one or more mechanical sensors, e.g., force transducers, pressure gauges, and/or motion sensors, are coupled in a vicinity of the heart, and send mechanical-sensor signals to the control unit indicative of aspects of the segment's motion and, optionally, of the motion or other mechanical parameters of other areas of the heart. The mechanical-sensor signals serve as feedback to enable the control unit to iteratively adjust the electrical signals applied to the heart and to compare newly-measured signals with desired values. Alternatively or additionally, other sensors (such as sensing electrodes, blood pressure or flow sensors) are coupled to the heart or elsewhere on the patient's body, and send signals to the control unit which are used in determining whether to modify parameters of the contractility control signals. Preferably, these signals are monitored continuously (particularly in embodiments in which the control unit comprises an external console) to ensure that the patient's vital signs are maintained within a predetermined, safe range.

Further alternatively or additionally, the control unit uses some of the sensor signals to determine an onset of arrhythmia, and modifies or terminates application of the contractility control signals responsive to the determination. In a preferred embodiment, pacemaking, cardioversion and/or defibrillation capabilities are additionally incorporated into the stimulator.

Preferably, the transition from the high phase to the low phase of the contractility control signals increases the contraction force of the segment within a very short period (typically about 1 second), and maintains the segment's increased contraction force for a prolonged period. For example, a high phase lasting 30 seconds may be followed by an increased contraction force which lasts for over 1 minute. Correspondingly, a shorter high phase is typically associated with a shorter period of increased contraction.

Suitable signals, apparatus, and methods for use in the context of preferred embodiments of the present invention are further described in two other U.S. patent applications, filed on even date, entitled "Local cardiac motion control using applied electrical signals," and "Induction of cardioplegia using applied electrical signals," which are assigned to the assignee of the present patent application and are incorporated herein by reference.

Although preferred embodiments are described in this application with reference to applying contractility control signals to modify the behavior of heart muscle, it is within the scope of the present invention to apply contractility control signals to other muscles, such as smooth muscle or skeletal muscle, mutatis mutandis.

There is therefore provided, in accordance with a preferred embodiment of the present invention, a method for controlling a segment of excitable tissue, the segment having an intrinsic activity level, the method including:

during a high phase, applying electrical energy of a given amplitude to the segment; and during a low phase, reducing the amplitude of the electrical energy applied to the segment relative to that applied during the high phase, so that the segment's activity level increases during the low phase above the intrinsic activity level.

Preferably, the tissue includes muscle tissue, wherein at the intrinsic activity level, the segment generates a first force of contraction, and reducing the amplitude during the low phase causes a second force to be generated in the segment that is greater than the first force. Further preferably, the tissue includes tissue of a heart, wherein cardiac output and/or blood pressure generated by the heart increases as a result of generating the second force.

In a preferred embodiment, applying the energy in the high phase includes generating an electric field in the segment which substantially does not cause contraction of muscle tissue in the segment. Typically, generating the field includes injecting into the segment electrical current at a generally constant rate, the current having a magnitude below a current threshold for inducing a contraction of muscle of the segment.

Preferably, the tissue includes tissue of a heart, wherein applying the electrical energy in the high phase comprises applying energy to a plurality of segments of the heart in respective high phases, each segment having a respective intrinsic activity level, and wherein reducing the amplitude during the low phase comprises reducing the amplitude of the electrical energy applied to each of the segments in a respective low phase, so that the activity levels of the segments increase above their intrinsic activity levels.

Further preferably, applying the energy in the high phases to the plurality of segments includes applying a first waveform to a first one of the segments and applying a second waveform, which differs from the first waveform, to a second one of the segments. Still further preferably, applying the energy in the high phases to the segments includes timing the application of the energy such that the high phase energy for one of the segments is applied to that segment while the low phase energy for another one of the segments is applied to the other segment.

In a preferred embodiment, the high and low phases of the energy are applied for substantially continuous periods longer than 10 seconds.

Preferably, the high and low phases of the energy are applied repeatedly, in order to increase an average contraction force of the segment.

Further preferably, the method includes sensing a physiological parameter, for example, a parameter reflecting motion of a portion of the heart, and the method further includes modifying a characteristic of the application of the electrical energy responsive to the parameter.

In a preferred embodiment, the method includes:

sensing activity of the heart to detect arrhythmia thereof; and applying antiarrhythmic electrical energy to the heart to treat the arrhythmia.

Preferably, applying the high phase energy decreases the activity level below the intrinsic activity level.

Most preferably, reducing the amplitude of the energy during the low phase comprises substantially discontinuing application of the energy.

Preferably, an average activity level of the segment over a period of at least one minute including the high and low phases is substantially greater than the intrinsic activity level.

There is further provided, in accordance with a preferred embodiment of the present invention, apparatus for controlling a segment of excitable tissue of a patient, the segment having an intrinsic activity level, the apparatus comprising:

one or more electrodes, coupled to the segment; and a control unit, which actuates the electrodes to apply electrical energy of a given amplitude to the segment during a high phase, and actuates the electrodes during a low phase to reduce the amplitude of the electrical energy applied to the segment relative to the energy applied during the high phase, so that the segment's activity level increases during the low phase above the intrinsic activity level.

Preferably, the tissue includes muscle tissue, wherein at the intrinsic activity level, the segment generates a first force of contraction, and wherein during the low phase, a second force is generated in the segment that is greater than the first force.

Most preferably, the tissue includes tissue of a heart, wherein the electrodes are coupled to a plurality of segments of the heart, each segment having a respective intrinsic activity level, and wherein the control unit actuates the electrodes to apply the electrical energy to the segments in respective high phases, and reduces the amplitude of the energy applied to the segments during respective low phases, so as to increase the activity levels of the segments above their respective first activity levels.

In a preferred embodiment, the apparatus includes at least one sensor coupled to the patient's body, which sensor senses a physiological parameter and conveys to the control unit a sensor signal responsive thereto, wherein the control unit modifies responsive to the sensor signal a characteristic of at least one of: the application of the energy in the high phase and the application of the energy in the low phase. Preferably, the sensor is selected from the list consisting of: a motion sensor, an accelerometer, a force transducer, an ECG sensor, a left ventricular pressure sensor, a blood pressure sensor, a pO2 sensor, a pCO2 sensor, an electrical activity sensor, and a blood flow rate sensor.

Preferably, the tissue includes tissue of a heart, wherein the sensor conveys a signal responsive to arrhythmia of the heart, and wherein the control unit applies antiarrhythmic energy to the heart to treat the arrhythmia.

In a preferred embodiment, the control unit applies pacing pulses to the electrodes so as to pace the heart.

Preferably, the control unit is implanted in the body of the patient. Alternatively, the control unit comprises a console external to the body of the patient.

The present invention will be more fully understood from the following detailed description of the preferred embodiments thereof, taken together with the drawings, in which:

DETAILED DESCRIPTION OF PREFERRED EMBODIMENTS

Figure 1:
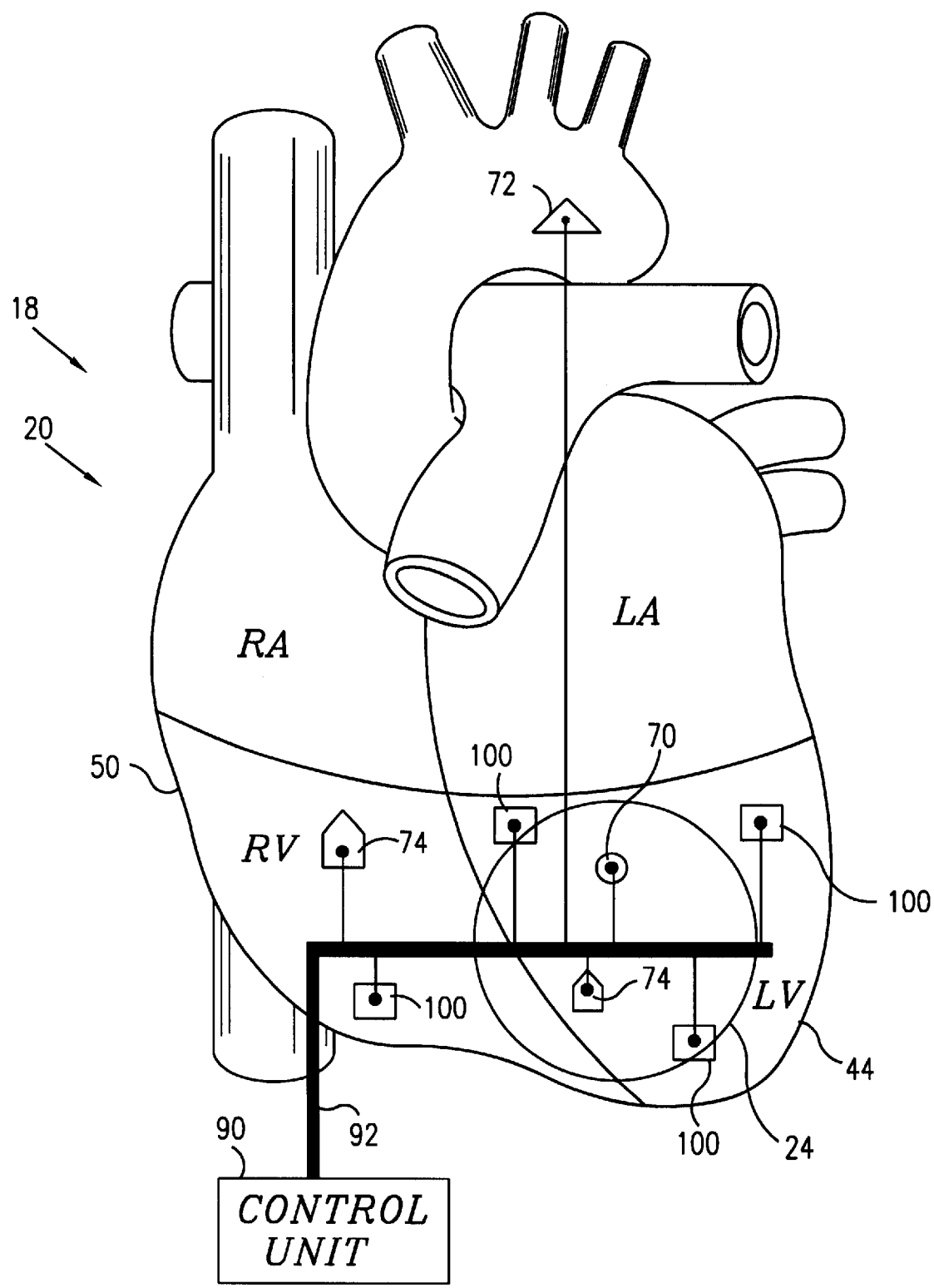
FIG. 1 is a schematic illustration of the external surface of a heart, showing the placement of electrodes thereon, in accordance with a preferred embodiment of the present invention.

FIG. 1 is a schematic illustration of cardiac stimulation apparatus 18, which controls contraction of a segment 24 of a patient's heart 20, in accordance with a preferred embodiment of the present invention. Apparatus 18 comprises an implantable or external control unit 90, which applies electrical energy in successive high and low phases through one or more electrodes 100 in a vicinity of segment 24, leading to an overall increase in an activity level of the segment.

Electrodes 100 are typically coupled to the epicardium 50 overlying left ventricle 44, within segment 24 or in a vicinity thereof. Alternatively or additionally, electrodes 100 may also be coupled to the endocardium or to other locations in or on the patient's body. In some applications, it is desirable to insert one or more of electrodes 100 into a blood vessel of or in a vicinity of the heart.

Control unit 90 is also optionally coupled to one or more local sense electrodes 74, which are placed on or in the heart and convey electrical signals responsive to cardiac electric activity. Additionally, one or more optional motion sensors 70 (e.g., accelerometers), coupled to the control unit, are placed on the heart, preferably in a vicinity of segment 24. Further additionally, one or more optional supplemental sensors 72 (e.g., blood pressure, pCO2, pO2, force transducers, and flow rate sensors) are coupled to the control unit and are placed on or in the heart or elsewhere on or in the patient's body. The control unit modifies the energy applied through electrodes 100 responsive to signals from sensors 70 and 72 and local sense electrodes 74, as described hereinbelow. Preferably, control unit 90 and the above-mentioned electrodes and sensors are permanently or semi-permanently implanted in or coupled to the patient's body.

The placement and number of electrodes and sensors are shown in FIG. 1 by way of example. Other sites on the heart or in a vicinity thereof are appropriate for electrode and sensor placement in other applications of the present invention. Different types of electrodes known in the art are typically selected based on the specific condition of the patient's heart, and may comprise coil, defibrillation, screw, patch, basket, needle and/or wire electrodes, or substantially any other electrode known in the art of electrical stimulation or sensing in tissue.

Figure 2:
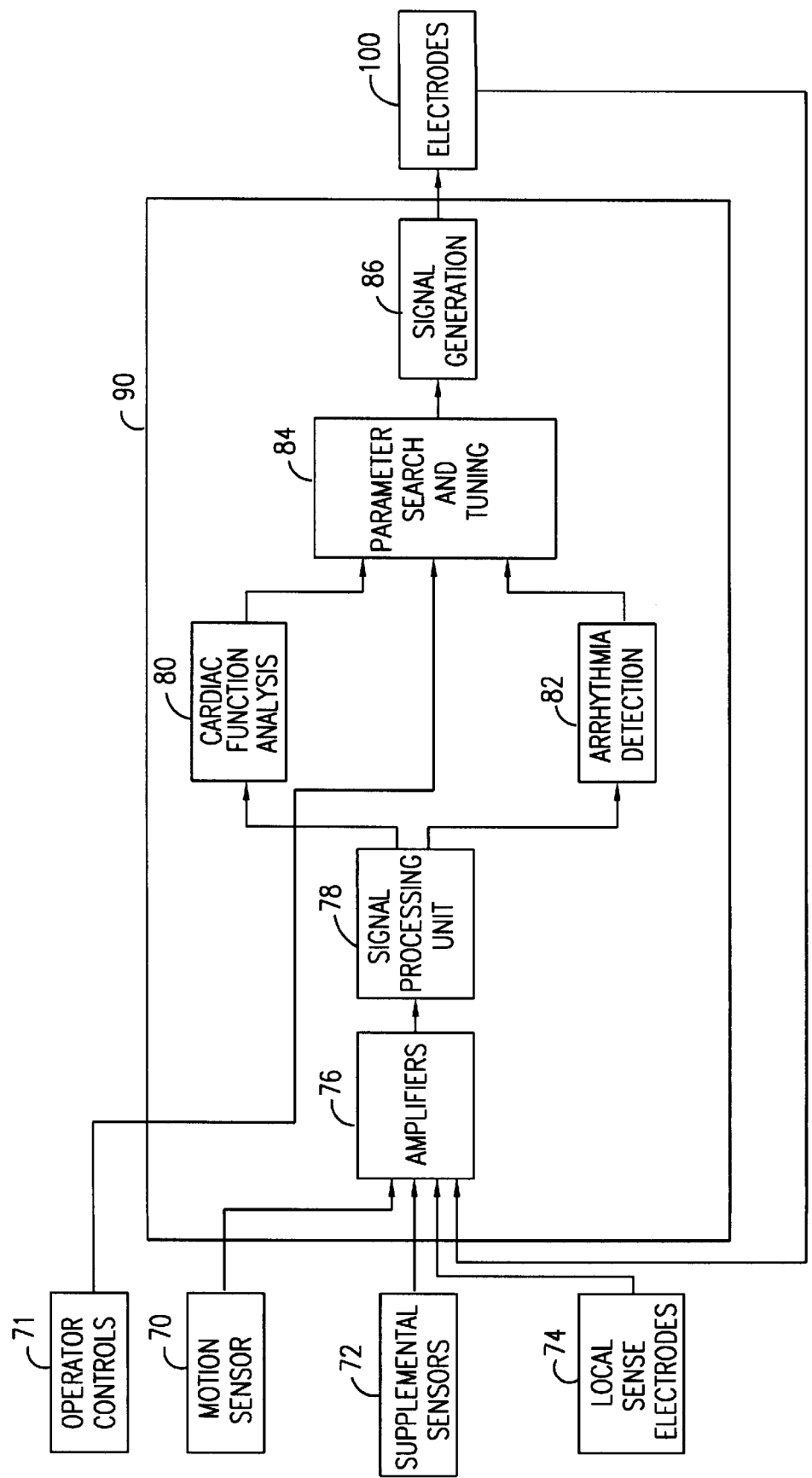
FIG. 2 is a schematic block diagram of a control unit, which generates signals to be applied to the electrodes shown in FIG. 1, in accordance with a preferred embodiment of the present invention.

FIG. 2 is a schematic block diagram of control unit 90, in accordance with a preferred embodiment of the present invention. Motion sensors 70, supplemental sensors 72, local sense electrodes 74, and electrodes 100 are preferably coupled to provide feedback signals to a cardiac function analysis block 80 of control unit 90. The feedback signals generally provide information about various aspects of the heart's performance to block 80, which analyzes the signals and actuates control unit 90 to modify the electrical energy applied to the heart responsive to the analysis. Preferably, the electrical energy comprises signals, typically pulses, which are adjusted by the control unit responsive to the feedback signals in order to yield a desired response, e.g., a predetermined blood pressure, blood oxygen level, cardiac output and/or electrical and motion profile of segment 24. Some forms of electrical signals appropriate for use in applying the present invention are described hereinbelow with reference to FIG. 3.

Preferably, block 80 conveys results of its analysis to a "parameter search and tuning" block 84 of control unit 90, which iteratively modifies characteristics of the electrical signals in order to attain a desired response. Block 84 typically utilizes multivariate optimization and control methods known in the art in order to cause one or more of the aforementioned mechanical, electrical, chemical and/or other measured parameters to converge to desired values. For the purposes of the present invention, block 84 typically modifies a set of controllable parameters (e.g., signal timing, magnitude and shape) responsive to the measured parameters in accordance with values in a look-up table and/or pre-programmed formulae stored in an electronic memory of control unit 90. Preferably, the controllable parameters are conveyed by block 84 to a signal generation block 86 of control unit 90, which generates, responsive to the parameters, electrical signals that are applied by electrodes 100 to the various sites on heart 20. Block 86 preferably comprises amplifiers, isolation units, and other standard circuitry known in the art of electrical signal generation.

An initial calibration procedure performed by a physician is preferably provided, in which, for example, parameter search and tuning block 84 modifies a characteristic (e.g., timing, magnitude, or shape) of signals applied through one of electrodes 100, and then determines whether a predetermined cardiac functional response generally improves following the modification. In a series of similar calibration steps, block 84 repeatedly modifies characteristics of the signals applied through each of electrodes 100, such that those modifications that improve the response are generally maintained, and modifications that cause it to worsen are typically eliminated or avoided. This procedure may similarly be followed at intermittent follow-up visits, and may also be performed by unit 90 automatically during regular use of the apparatus (e.g., daily). When apparatus 18 is calibrated in the presence of a physician, it is often desirable to have the patient perform increasing levels of exercise (e.g., walk on a treadmill), in order to derive a broader range of operating parameters that are stored in control unit 90 and can be accessed responsive to signals from the sensors and local sense electrodes.

Most preferably, during calibration and during regular operation of control unit 90, an arrhythmia detection block 82 of control unit 90 receives inputs from sensors 70 and 72 and electrodes 74 and 100, and/or other electrodes and sensors (not shown), and evaluates these inputs to detect an onset of cardiac arrhythmia. Preferably, block 82 employs techniques known in the art for determining arrhythmia, so that parameter search and tuning block 84 can treat or terminate the arrhythmia by applying, for example, regular pacing pulses or defibrillation pulses.

Sensors 70 typically comprise one or more accelerometers, which produce electric fields responsive to acceleration thereof. Control unit 90 preferably comprises: (a) amplifiers 76 to amplify low-level signals generated by motion sensors 70, supplemental sensors 72 and local sense electrodes 74; and (b) a signal processing unit 78, coupled to the amplifiers, which conveys representative signals to cardiac function analysis block 80 and arrhythmia detection block 82.

Figure 3:
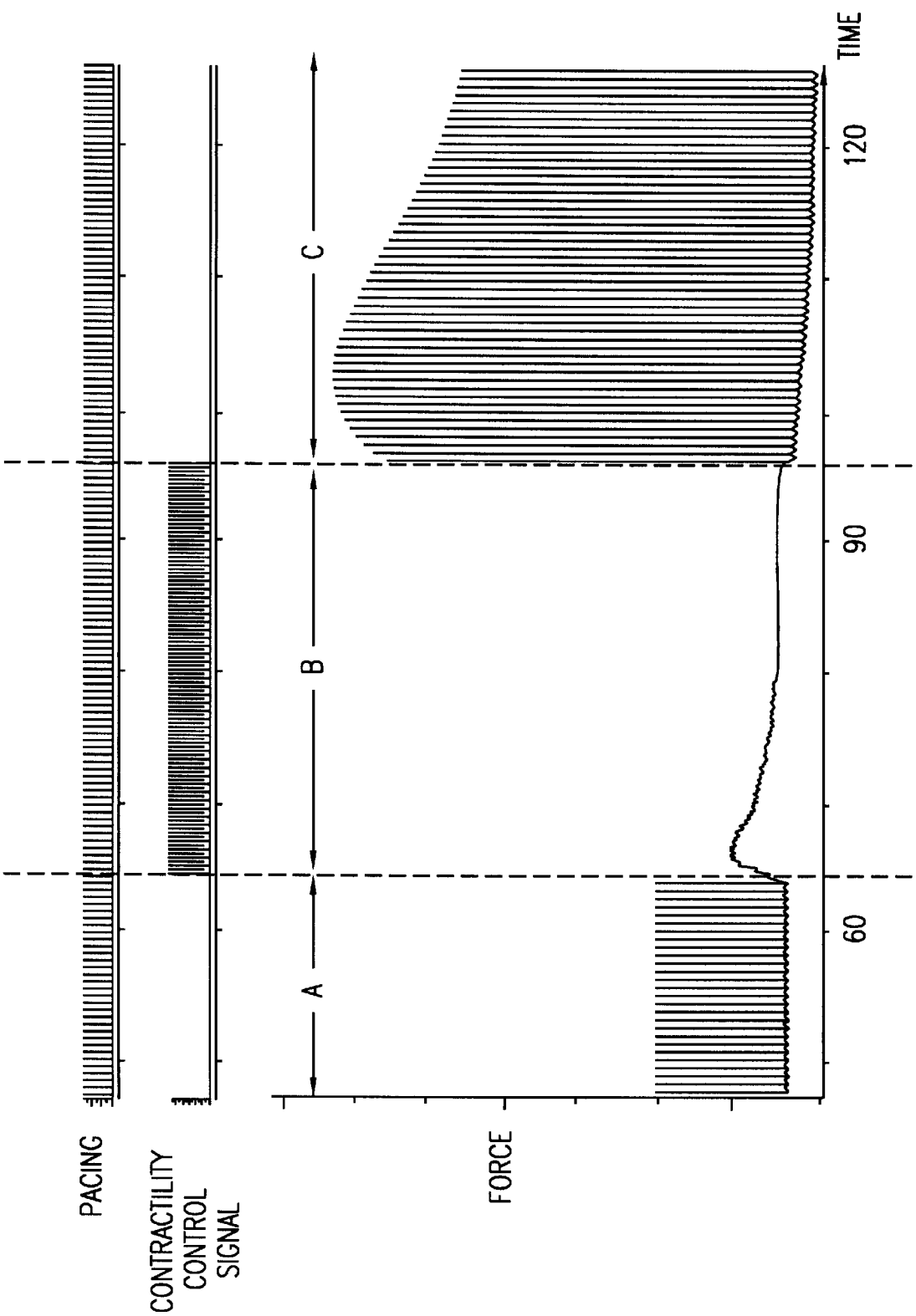
FIG. 3 schematically illustrates electrical signals applied to papillary muscle, in accordance with a preferred embodiment of the present invention, and experimental results obtained by application of the signals.

FIG. 3 schematically illustrates pacing and contractility control signals applied to in vitro mammalian papillary muscle, in accordance with a preferred embodiment of the present invention, and experimental results obtained by application of the signals. Pacing pulses having amplitudes of about 1 mA and widths of approximately 2 msec were applied at approximately 2 Hz to the muscle tissue during a warm-up, control period "A," whose duration was greater than 1 minute. Force generated by the muscle responsive to the pacing was measured, and is seen in FIG. 3 to have generally constant twitch force throughout the control period. During periods "B" and "C," respective high and low phases of contractility control signals as provided by the present invention were applied to the muscle tissue. The high phase was characterized by rapid sinusoidal pacing pulses, applied at 28 Hz with a 50% duty cycle. Each pulse had a 2 mA amplitude and a 2.5 mA DC offset.

In this experiment, the high-phase signal produced a marked decrease in the generated twitch force, to less than 10% of that during period "A" within 2 seconds. Within 15 seconds of initiation of the high phase, the measured force dropped to a low, constant plateau level.

In the low phase of this experiment (period "C"), substantially no contractility control current or voltage was applied to the muscle tissue. Administration of pacing pulses continued. As shown in FIG. 3, the transition from the high phase to the low phase was characterized by an almost immediate increase in the measured twitch force in the tissue, to approximately three times the peak force developed during control period "A." The force during period "C" is seen in FIG. 3 to remain over two times the force during period "A" for more than 30 seconds, and preferably remains above the level of period "A" for over 1 minute (not shown). It is clear that the overall force, time-integrated over periods "B" and "C," is significantly greater than that which would have been attained without application of the contractility control signals.

It is noted (but not shown in the figures) that shorter durations of the high phase produce correspondingly shorter periods of increased contraction force. This can be used to advantage in applications wherein, for example, multiple segments are stimulated with contractility control signals in sequence, and it is desired that each segment produce a relatively brief, enhanced contraction, in order to increase overall cardiac output.

Preferably, the average power output of muscle tissue exposed to repeated application of contractility control signals is greater than that generated responsive to either standard pacing pulses (like those applied during period "A") or natural cardiac activity in an in vivo heart. Thus, application of contractility control signals as provided by the present invention is appropriate, for example, for assisting a heart that is otherwise unable to satisfy immediate physiological requirements of flow rate and blood pressure. In particular, contractility control signals may be applied to one or more segments of the heart, in a generally localized region, which may be a functional or a dysfunctional area of one chamber, or in multiple chambers of the heart. Contractility control signals applied to different segments are preferably timed with respect to each other so that during a time period when some segments are exposed to the high phase of the signals, and thus do not contribute substantially to the heart's pumping action, the rest of the heart muscle is generally either contracting normally, or in an enhanced manner responsive to application of low-phase contractility control signals.

Typically, parameters of the contractility control signals, such as shape, magnitude, frequency, DC offset, uniphasic and biphasic aspects, absolute durations of the high and low phases, and ratio of the durations of the high and low phases, are selected in order to increase the heart's output. For example, in some stimulation modes, increasing the duration of the high phase increases the magnitude of the force generated during the low phase. Although the contractility control signal is shown in FIG. 3 as being a sequence of 28 Hz sinusoidal pulses, other shapes as known in the art of electrical stimulation of tissue are included within the scope of the present invention.

In general, each one of electrodes 100 may convey a particular waveform to heart 20, differing in certain aspects from the waveforms applied by the other electrodes. The particular waveform to be applied by each electrode is determined by control unit 90, preferably under the control of a human operator, at least in an initial calibration procedure, as described hereinabove. Aspects of the waveforms which are set by the control unit, and may differ from electrode to electrode, typically include parameters such as time shifts between application of waveforms at different electrodes, waveform shapes, amplitudes, DC offsets, durations, frequencies and duty cycles. For example, although the waveforms applied to many of electrodes 100 usually comprise a series of monophasic square wave pulses, other waveforms, such as a sinusoid, a series of biphasic square waves, or a waveform including an exponentially-varying characteristic, could be applied to the rest of electrodes 100. Additionally, in some operational modes, the voltage applied by some or all of electrodes 100 is controlled, rather than the current, as described hereinabove. Generally, the shape, magnitude, and timing of the waveforms are optimized for each patient, using suitable optimization algorithms as are known in the art, in order to attain a desired set of feedback values, as described hereinabove with reference to FIG. 2.

Application of contractility control signals is typically, but not necessarily, accompanied by artificial pacing pulses, as shown in FIG. 3. In some operational modes, however, the sinoatrial node generates the cardiac rhythm, substantially without externally-applied pacing. In such modes, local sense electrodes 74 and, optionally, some or all of electrodes 100 convey electrical signals to control unit 90, so as to enable parameter search and tuning block 84 to synchronize the electrical signals applied by electrodes 100 with the natural electrical activity of the heart. It will be understood that although electrodes 74 and 100 are shown for clarity of explanation as separate entities, a single set of electrodes may be used to perform both functions.

Although preferred embodiments are described in this application with reference to applying contractility control signals to modify the behavior of heart muscle, it is within the scope of the present invention to apply contractility control signals to other muscles, such as smooth muscle or skeletal muscle, mutatis mutandis. For example, incomplete paralysis and autonomic dysfunction following spinal cord injury may be treated by using contractility control signals to increase an overall power output of affected skeletal and smooth muscle tissue. Additionally, contractility control signals may be applied to injured muscle tissue, in order to provide; (a) relatively-long rest periods, which improve healing of the muscle; and (b) intermittent "exercise" periods, which prevent atrophy of the muscle. It will thus be appreciated that the preferred embodiments described above are cited by way of example, and the full scope of the invention is limited only by the claims.

What is claimed is:

1. A method for controlling a segment of excitable muscle tissue, the segment having an intrinsic activity level, at which intrinsic activity level the segment generates a first force of contraction, the method comprising:

during a high phase, applying electrical energy of a given amplitude to the segment; and during a low phase, reducing the amplitude of the electrical energy applied to the segment relative to that applied during the high phase, so that the segment's activity level increases during the low phase above the intrinsic activity level, and causes a second force to be generated in the segment that is greater than the first force.

2. A method for controlling a segment of excitable muscle tissue of a heart having a cardiac output caused by a first force of contraction of the segment at an intrinsic activity level thereof, the method comprising:

during a high phase, applying electrical energy of a given amplitude to the segment; and during a low phase, reducing the amplitude of the electrical energy applied to the segment relative to that applied during the high phase, so that the segment's activity level increases during the low phase above the intrinsic activity level, and causes a second force to be generated in the segment that is greater than the first force, such that the cardiac output increases as a result of the segment generating the second force.

3. A method for controlling a segment of excitable muscle tissue of a heart having an intrinsic activity level, at which intrinsic activity level the segment generates a first force of contraction, the method comprising:

during a high phase, applying electrical energy of a given amplitude to the segment; and during a low phase, reducing the amplitude of the electrical energy applied to the segment relative to that applied during the high phase, so that the segment's activity level increases during the low phase above the intrinsic activity level, and causes a second force to be generated in the segment that is greater than the first force, such that blood pressure generated by the heart increases as a result of the segment generating the second force.

4. A method for controlling a segment of excitable tissue, the segment having an intrinsic activity level, the method comprising:

during a high phase, injecting current into the segment at a generally constant rate which is below a threshold for inducing a contraction of muscle tissue of the segment, so as to generate an electric field in the segment which substantially does not cause contraction of the muscle tissue; and during a low phase, reducing the rate of injection of the current relative to the rate of injection during the high phase, so that the segment's activity level increases during the low phase above the intrinsic activity level.

5. A method for controlling a plurality of segments of excitable tissue of a heart, each segment having a respective intrinsic activity level, the method comprising:

during respective high phases, applying electrical energy of respective given amplitudes to the plurality of segments; and during respective low phases, reducing the amplitude of the electrical energy applied to each of the segments, so that the activity levels of the segments increase during the respective low phases above their respective intrinsic activity levels.

6. A method according to claim 5, wherein applying the energy in the high phases to the plurality of segments comprises applying a first waveform to a first one of the segments and applying a second waveform, which differs from the first waveform, to a second one of the segments.

7. A method according to claim 5, wherein applying the energy in the high phases to the segments comprises timing the application of the energy such that the high phase energy for one of the segments is applied to that segment while the low phase energy for another one of the segments is applied to the other segment.

8. A method for controlling a segment of excitable tissue, the segment having an intrinsic activity level, the method comprising:

during a high phase, applying energy of a given amplitude to the segment for a substantially continuous period longer than 10 seconds; and during a low phase, reducing the amplitude of the electrical energy applied to the segment relative to that applied during the high phase, so that the segment's activity level increases during the low phase above the intrinsic activity level.

9. A method for controlling a segment of excitable tissue, the segment having an intrinsic activity level, the method comprising:

during a high phase, applying electrical energy of a given amplitude to the segment; and during a low phase, extending for a substantially continuous period longer than 10 seconds, reducing the amplitude of the electrical energy applied to the segment relative to that applied during the high phase, so that the segment's activity level increases during the low phase above the intrinsic activity level.

10. A method for controlling a segment of excitable tissue of a heart, the segment having an intrinsic activity level, the method comprising:

during a high phase, applying electrical energy of a given amplitude to the segment;

during a low phase, reducing the amplitude of the electrical energy applied to the segment relative to that applied during the high phase, so that the segment's activity level increases during the low phase above the intrinsic activity level;

sensing motion of a portion of the heart; and modifying, responsive to the sensing, a characteristic of the application of the electrical energy.

11. A method for controlling a segment of excitable tissue, the segment having an intrinsic activity level, the method comprising:

during a high phase, applying electrical energy of a given amplitude to the segment; and during a low phase, reducing the amplitude of the electrical energy applied to the segment relative to that applied during the high phase, so that the segment's activity level increases during the low phase above the intrinsic activity level, such that an average activity level of the segment over a period of at least one minute including the high and low phases is substantially greater than the intrinsic activity level.

12. Apparatus for controlling a segment of excitable muscle tissue, the segment having an intrinsic activity level, at which intrinsic activity level the segment generates a first force of contraction, the apparatus comprising:

one or more electrodes, adapted to be coupled to the segment; and a control unit, adapted to actuate the electrodes to apply electrical energy of a given amplitude to the segment during a high phase, which is followed by a low phase, during which low phase the control unit is adapted to reduce the amplitude of the electrical energy applied to the segment relative to the energy applied during the high phase, so that the segment's activity level increases during the low phase above the intrinsic activity level and a second force is generated in the segment that is greater than the first force.

13. Apparatus according to claim 12, wherein the electrodes are adapted to be coupled to a segment of excitable muscle tissue of a heart having a cardiac output, and wherein the control unit is adapted to reduce the amplitude of the energy such that the cardiac output increases as a result of the second force generated in the segment of the heart.

14. Apparatus according to claim 12, wherein the electrodes are adapted to be coupled to a segment of excitable muscle tissue of a heart, and wherein the control unit is adapted to reduce the amplitude of the energy such that blood pressure generated by the heart increases as a result of the second force generated in the segment of the tissue of the heart.

15. Apparatus for controlling a plurality of segments of excitable tissue of a heart, each segment having a respective intrinsic activity level, the apparatus comprising:

a plurality of electrodes, adapted to be coupled respectively to the plurality of segments; and a control unit, adapted to actuate the electrodes to apply electrical energy of respective given amplitudes to the segments in respective high phases, and to reduce the respective amplitudes of the energy applied to the segments during respective low phases, so as to increase the activity levels of the segments above their respective intrinsic activity levels.

16. Apparatus for controlling a segment of excitable tissue of a patient, the segment having an intrinsic activity level, the apparatus comprising:

one or more electrodes, adapted to be coupled to the segment; and a control unit, adapted to actuate the electrodes to apply electrical energy of a given amplitude to the segment during a high phase, which is followed by a low phase, during which low phase the control unit is adapted to reduce the amplitude of the electrical energy applied to the segment relative to the energy applied during the high phase, so that the segment's activity level increases during the low phase above the intrinsic activity level, and such that an average activity level of the segment over a period of at least one minute including the high and low phases is substantially greater than the intrinsic activity level.

17. Apparatus for controlling a segment of excitable tissue of a patient, the segment having an intrinsic activity level, the apparatus comprising:

one or more electrodes, adapted to be coupled to the segment; and a control unit comprising a console external to the body of the patient, the control unit being adapted to actuate the electrodes to apply electrical energy of a given amplitude to the segment during a high phase, which is followed by a low phase, during which low phase the control unit is adapted to reduce the amplitude of the electrical energy applied to the segment relative to the energy applied during the high phase, so that the segment's activity level increases during the low phase above the intrinsic activity level.

* * * * *